United States Patent [19]
Brain

[11] Patent Number: 5,632,271
[45] Date of Patent: May 27, 1997

[54] LARYNGEAL MASK WITH GASTRIC-DRAINAGE FEATURE

[76] Inventor: Archibald I. J. Brain, Sandford House, Fan Court Gardens, Longcross Road, Chertsey, Surrey, United Kingdom, KT16 0DJ

[21] Appl. No.: 622,734

[22] Filed: Mar. 27, 1996

[30] Foreign Application Priority Data

Mar. 22, 1996 [GB] United Kingdom ........... 9606012

[51] Int. Cl.$^6$ ................................................. A61M 16/00
[52] U.S. Cl. ................. 128/207.15; 604/96; 604/176; 128/207.14
[58] Field of Search .................. 128/207.15, 207.14, 128/206.26, 207.16, 200.26

[56] References Cited

U.S. PATENT DOCUMENTS

| | | | |
|---|---|---|---|
| 4,509,514 | 4/1985 | Brain | 128/207.15 |
| 4,995,388 | 2/1991 | Brain | 128/207.15 |
| 5,241,956 | 9/1993 | Brain | 128/207.15 |
| 5,249,571 | 10/1993 | Brain | 128/207.14 |
| 5,282,464 | 2/1994 | Brain | 128/207.15 |
| 5,297,547 | 3/1994 | Brain | 128/207.15 |
| 5,303,697 | 4/1994 | Brain | 128/200.26 |
| 5,355,879 | 10/1994 | Brain | 128/207.15 |

FOREIGN PATENT DOCUMENTS 2205499 12/1988 United Kingdom .......... A61M 16/04

*Primary Examiner*—Vincent Millin
*Assistant Examiner*—Robert N. Wieland
*Attorney, Agent, or Firm*—Hopgood, Calimafde, Kalil & Judlowe

[57] ABSTRACT

A laryngeal-mark airway device has additional provision for extraction of gastric discharges while the mask seals the airway to the laryngeal inlet. A single elongate flexible small-bore drainage tube is so bonded to the posterior curvature of an elongate flexible airway as to enhance torsional stiffness in the combined airway tube and drainage tube. The airway tube has a customary fit to the air inlet of the domed backing plate of the mask, and a generally elliptical inflatable ring around the backing plate and lumen of the mask is configured to establish a continuous peripherally sealed engagement to the laryngeal inlet. The elongate flexible drainage tube has sealed entry into the distal end of the inflatable ring, distally traversing the same with sealed distal exit from the distal end of the inflatable ring. The distal end of the inflatable ring is so configured that, despite drainage-tube passage within and through the distal end of the inflatable ring, the inflatable capacity of the distal end of the inflatable ring remains substantially the same as for the full peripheral course of the inflatable ring.

18 Claims, 1 Drawing Sheet

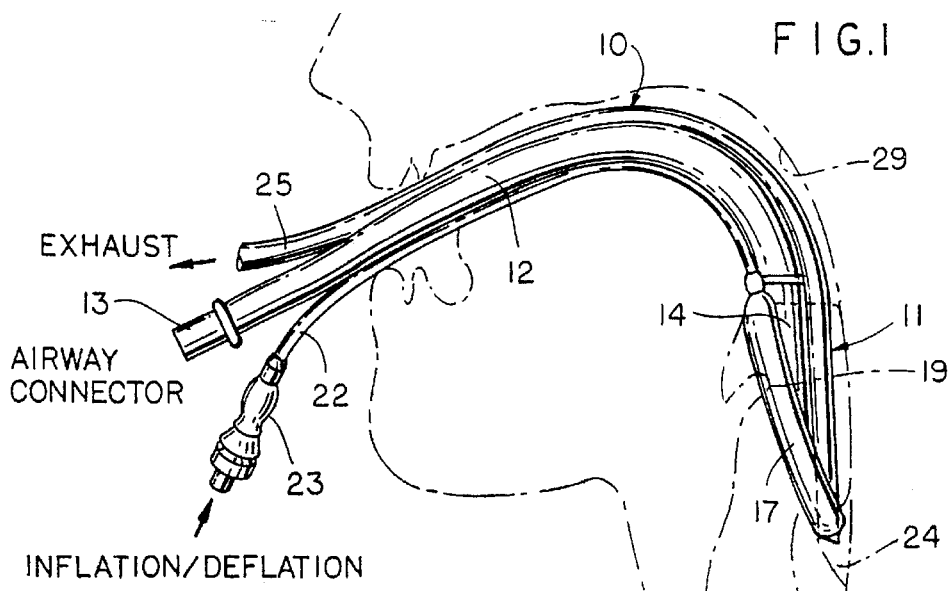
FIG.1
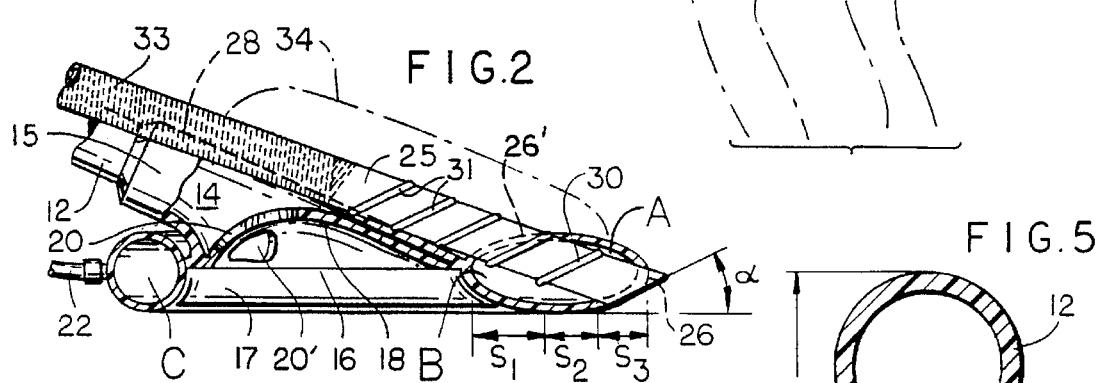
FIG.2
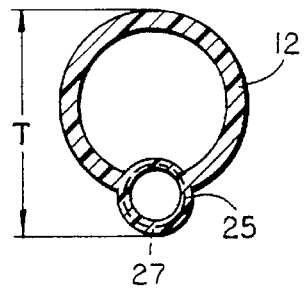
FIG.5
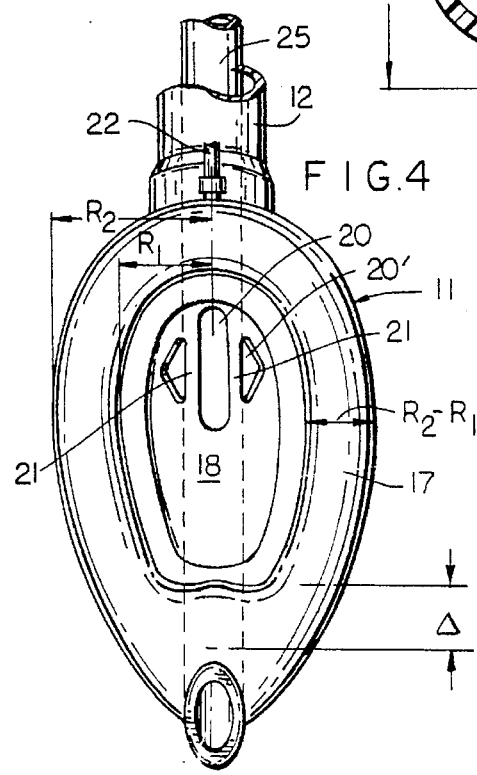
FIG.3
FIG.4

5,632,271

LARYNGEAL MASK WITH GASTRIC-DRAINAGE FEATURE

BACKGROUND OF THE INVENTION

This invention relates to an artificial-airway device capable of establishing sealed application to the laryngeal inlet for ventilating the lungs of a patient and having the further feature of providing drainage of gastric fluid without impairing the ventilating effectiveness of the airway.

Artificial airway devices of the character indicated, but without provision for drainage of a gastric discharge, are exemplified by the disclosures of U.S. Pat. No. 4,509,514; U.S. Pat. No. 5,249,571; U.S. Pat. No. 5,282,464; U.S. Pat. No. 5,297,547; U.S. Pat. No. 5,303,697; and by the disclosure of UK patent 2,205,499. Such devices with additional provision for gastric-discharge drainage are exemplified by U.S. Pat. No. 4,995,388 (FIGS. 7 to 10); U.S. Pat. No. 5,241,956; and U.S. Pat. No. 5,355,879.

In general, such devices aim to provide an airway tube of such cross-section as to assure more than ample ventilation of the lungs, and the designs with provision for gastric drainage have been characterized by relatively complex internal connections and cross-section calculated to serve in difficult situations where substantial solids could be present in a gastric discharge. As a result, the provision of a gastric discharge opening at the distal end of the mask and applicable for direct service of the hypopharynx has been bulky and unduly stiff, thus making for difficulty in properly inserting the mask down the patient's throat. Moreover, undue bulk and stiffness are at cross-purposes to the distal flexibility required for tracking the posterior curvature of the patient's throat, in such manner as to reliably avoid traumatic encounter with the epiglottis and other natural structures of the pharynx.

In most cases of aid to be administered inter alia by relatively unskilled personnel of first-aid and rescue squads, the real need is for relatively simple structure which can be quickly installed to establish a sealed airway passage, and at minimum incremental cost or complexity of installation to provide at least an ability to drain a liquid gastric discharge, virtually as soon as the airway passage has been sealed.

BRIEF STATEMENT OF THE INVENTION

It is a principal object of the invention to provide an improved laryngeal-mask device with at least some provision for drainage of a liquid gastric discharge without impairing the sealing effectiveness of the device around the laryngeal inlet.

It is a specific object to meet the above object with structure of elemental simplicity and lower cost.

Another specific object is to meet the above objects with airway-masking structure which can be safely and properly installed, using relatively unskilled personnel.

The invention achieves these objects with a laryngeal-mask device, in which a single elongate flexible small-bore drainage tube is so bonded to the posterior curvature of an elongate flexible airway as to enhance torsional stiffness in the combined airway tube and drainage tube. The airway tube has a customary fit to the air inlet of the domed backing plate of the mask, and a generally elliptical inflatable ring around the backing plate and lumen of the mask is configured to establish a continuous peripherally sealed engagement to the laryngeal inlet. The elongate flexible drainage tube has sealed entry into the distal end of the inflatable ring, distally traversing the same with sealed distal exit from the distal end of the inflatable ring. The distal end of the inflatable ring is so configured that, despite drainage-tube passage within and through the distal end of the inflatable ring, the inflatable capacity of the distal end of the inflatable ring remains substantially the same as for the full peripheral course of the inflatable ring.

Various further features are optional in combination with the indicated sectional consistency within the inflatable ring throughout its peripheral course.

BRIEF DESCRIPTION OF THE DRAWINGS

A presently preferred embodiment of the invention will be described in detail, in conjunction with the accompanying drawings, in which:

FIG. 1 is a simplified diagram in side elevation to show a laryngeal mask assembly of the invention, with mask structure at the distal end of the assembly in installed position in a patient;

FIG. 2 is an enlarged, fragmentary, and partly broken-away side elevation of mask construction in FIG. 1;

FIG. 3 is a plan view of the posterior or pharynx-exposed side of the mask construction of FIG. 2;

FIG. 4 is a plan view of the anterior or larynx-exposed side of the mask construction of FIGS. 2 and 3; and FIG. 5 is an enlarged sectional view taken at 5—5 in FIG. 3.

DETAILED DESCRIPTION

In FIG. 1 of the drawings, the preferred laryngeal-mask airway assembly 10 of the invention is seen to comprise mask structure 11 at the distal end of a flexible airway tube 12, which conforms to curvature of the patient's airway and extends to a proximal end 13 outside of the patient, the end 13 being adapted for connection to air or other ventilating apparatus for the patient's lungs.

The mask structure per se comprises a somewhat domed backing-plate member 14 with a proximally directed air-inlet formation 15 having exclusive communication with the distal end of airway tube 12; the direction of this airway connection is on an air-inlet axis that is inclined at an acute angle to the generally elliptical mounting rim 16 of the backing-plate member, and rim 16 lies generally in a geometric plane of peripherally continuous outer connection to an inflatable ring 17; it is convenient sometimes to refer to this geometric plane as the equatorial plane of inflatable ring 17 (i.e., of rim 16). Rim 16 has further peripheral connection to a softly flexible masking member 18 which is dome-shaped to comfortably accommodate the patient's epiglottis 19 when the mask structure 11 is installed position, and the masking member 18 establishes a lumen for patient ventilation through mask 11; in the form shown, the lumen comprises three elongate openings 20, 20', which are defined by two spaced longitudinal bars 21 (FIG. 4) that are integral formations of the masking member 18, the same being designed to prevent epiglottis blockage of ventilation via the mask, inflation/deflation of the flexible ring 17 is via a flexible tube 22 for connection (external of the patient) via check-valve means 23 to suitable pumping means, not shown but suggested by legend in FIG. 1.

As with other of my laryngeal-mask assemblies to date, the assembly 10, as thus-far described, is first fully deflated in preparation for manipulated insertion through the patient's mouth and throat, relying upon piloting guidance of the deflated distal lip of ring 17 along the curved upper (and progressively posterior) wall surfaces of the patient's airway in tracking contact with the back wall of the pharynx and insertional limitation at entry to the hypopharynx 24, i.e., without trauma to the upper sphincter of the oesophagus. The ring 17 is then inflated, to the point of establishing a peripheral seal of the laryngeal inlet.

It is a feature of the invention that a single, relatively small-bore flexible tube 25 (suitably of 1-mm wall thickness and with a bore diameter in the range of 6 to 8 mm) for extraction of a gastric discharge be so integrated into the assembly 10 as not only to contribute to relative torsional stiffness of an otherwise relatively flexible and considerably larger-bore airway tube but also to be per se relatively softly compliant in its passage along at least the distal half of backing plate 14, and through the distal end of inflatable ring 17; suitably, the outer diameter of flexible drainage tube 25 is at least no greater than substantially one-half the bore diameter of airway tube 12. Preferably, passage through the distal end of ring 17 is via a sealed, more proximal entry into ring 17, generally indicated in FIG. 2 by the longitudinal spread $S_m$, followed by a free longitudinal span $S_2$ within the inflatable distal volume of ring 17, and in turn followed by a sealed distal exit from ring 17 over the longitudinal spread $S_3$. Stated in other words, and taking the plane of rim 16 as being substantially the equatorial plane of the distal end of ring 17, the more proximal tube-25 entry over spread $S_1$ is generally above the equatorial plane of rim 16, and the distal tube-25 exit over spread $S_3$ is generally below the equatorial plane of rim 16.

For the foregoing conditions to be met, and further in order to permit inflation of ring 17 to establish its full peripheral sealing engagement around the laryngeal inlet, it is a feature of the invention that, in the arcuate region of its distal quadrant end, for the internal section area available for inflation air to perform its sealing function (with substantial consistency with respect to remaining quadrants of ring 17, the longitudinal section of the distal end of ring 17 is of elongate generally elliptical section as seen in FIG. 2; this elongate generally elliptical section is preferably such that the inflatable section area, namely, the section area remaining after account is taken of the occluding effect of the span and diameter of tube 25 in its passage through the distal end of ring, shall be substantially equal to the otherwise inflated circular section of ring 17, as seen at the proximal end of ring 17 in FIG. 2, or as designated $R_2-R_1$ in FIG. wherein $R_2$ and $R_1$ respectively designate maximum outer and minimum inner radial limits of the inflated ring 17 at any given right-section plane perpendicular to the plane of rim 16, for all quadrants of ring 17 except for the distal end of the ring, in inflated condition. In FIG. 4, the additional length or major-axis dimension of the inflated elliptical section is designated $\Delta$, meaning that said major-axis dimension is greater than the diameter of the otherwise circular inflated section areas in lateral and proximal quadrants of ring 17; the added inflatable length $\alpha$ will be seen also to correspondingly shorten the longitudinal extent of backing-plate member thus enhancing overall flexibility of the distal end of the mask per se. In FIG. 2, the legends A and B designate the distal section areas of ring 17, which taken together, provide a net section area that substantially accords with the inflated circular area C which characterizes the inflated ring 17 in said lateral and proximal quadrants.

It has been indicated above that the discharge tube 25 exits the distal end of ring 17, thus projecting the distally open end of tube 25 beyond the distal end of ring 17. The amount of such projection will be understood to be enough to permit application of a peripheral bead 26 of adhesive around tube 25 at exiting juncture with ring 17. The drawing of FIG. 2 indicates preference that such a bead shall be on a generally elliptical course by reason of juncture involving the cylindrical outer surface of tube 25 and the lower-right wall-section profile of the distal elliptical section of ring 17, in inflated condition, as seen in FIG. 2; a similar bead 26' will be understood to seal tube 25 to ring 17 (in inflated condition) at tube-25 entry into ring 17. As also seen in FIG. 2, the distally open end of tube 25 involves a slanted truncation of tube 25 at approximately 45 degrees to the axis of tube 25, and at an angle $\alpha$ in the range of 20 to 30 degrees to the equatorial plane of rim 16.

An adhesively secured "piggy-backing" of tube 25 to the outer curved profile of the airway tube 12, will provide reinforcement of the airway-tube curvature shown in FIG. 1 and with a degree of torsional stiffening of the thus-combined tubes 12/25. However, FIG. 5 illustrates a preference that the discharge tube 25 be integrated into a portion of the airway tube 12, thereby not only enhancing torsional stiffness for easy manipulation in the course of mask insertion into a patient but also entailing a lesser overall thickness T which is more readily accommodated between the patient's upper and lower front teeth. Once the proximal end of the mutually reinforced tubes 12/25 emerges from the patient's mouth, as seen in FIG. 1, tube 25 may branch away from the airway tube 12 so as to permit independent connection of the proximal ends of these tubes for service of their respective ventilation and gastro-exhaust purposes. Also, the described preference for the FIG. 5 combination of tubes 12/25 will be understood to signify that the backing-plate member 14 may be substantially reduced in bulk and stiffness as compared with prior constructions, in that its back-surface profile is now characterized by a longitudinal slot for adhesively sealed reception of the flexible discharge tube 25, the longitudinal profile of such reception being suggested by dashed line 28 in FIG. 2.

The laryngeal-mask airway assembly as thus far described with tube 25 for exhausting gastric fluid, will be seen to meet stated objectives. Manipulated insertion of the mask in deflated condition enables swift flexible tracking of the distal end of the truncated tubular end of the mask 11 along the posterior wall surface 29 of the patient's anatomical airway, without fouling the epiglottis and locating itself in the hypopharynx 24. Ring 17 can be quickly inflated to establish its peripherally continuous sealing engagement around the laryngeal inlet, and of course, the exhaust feature of tube 25 can then be quickly activated by external means (not shown). All parts may be of relatively softly compliant elastomeric material such as silicone rubber, illustratively of 30–40 durometer, except that tube 25 may be of commercially available tubing, suitably silicon rubber clear 40 duro, available from accused incorporated, of Merillville, Ind., U.S.A.

For virtually all situations, the relatively small bore of discharge tube 25 is such that inflation pressure within ring 17 does not so compress tube 25 as to choke off the gastric-discharge function; however, if one or more peripheral beads as at 30 are applied around tube 25 prior to assembling insertion into and through the inflatable elliptical section at the distal end of mask structure 11, then one gains reinforcement against any such collapse. As seen in FIG. 2, it is preferred that the reinforcing bead or beads (30) be axially spaced and slanted from the axis of tube 25 and generally parallel with the truncation at the distal end of tube 25. The slanted orientation of the bead or beads (30) will be seen to permit a degree of tube-25 collapse when ring 17 is deflated, all without degrading the flexibility desired in the distal half of the mask in deflated condition.

Further, and preferably, a back cushion 34 of flexible sheet material, also suitably of silicone rubber, is merely suggested by its longitudinal profile in inflated state in FIG. 2, the same being peripherally sealed to the back side of the mask, as suggested in FIG. 3 by the generally elliptical dashed-line peripheral course 35 of back-cushion attachment to the back of the mask structure 11.

For enhanced torsional stiffness of the combined tubes 12/25 in the proximal direction away from the more flexible distal half of the mask structure 11, FIG. 2 additionally shows schematically that the otherwise softly compliant tube 25 may incorporate torsionally stiffening reinforcement in the form of a closely wound helix of fine stainless-steel or nylon filament, suggested by closely adjacent dashed-line hatching 33 from the proximal half of the mask structure and extending continuously and in the proximal direction throughout the described combination of tubes 12/25, as in FIG. 5. And in the remaining unreinforced length of tube 25, i.e., between the distal end of filament 33 and the entry seal 26' to ring 17, further slanted and spaced beads 31, as at 30, may be used to assure resistance to collapse of tube 25 in the presence of back-cushion inflation pressure, even though use of the back cushion may so forwardly load inflated ring 17 into laryngeal-inlet seal effectiveness as to require a lower level of inflation-air pressure than if the back cushion were not provided. It is also to be noted that the above-described provision for added area of ring-17 material (determining internal section areas A and B in FIG. 2) is in itself a feature of enhanced assurance of a peripherally continuous seal of ring 17 around the laryngeal inlet.

What is claimed is:

1. A laryngeal mask airway system, comprising a generally elliptical inflatable ring of relatively softly compliant elastomeric material, said ring extending from a proximal end to a distal end, said ring being adapted for sealed application to the laryngeal inlet of a patient, and means including a backing-plate member of relatively stiffly compliant material peripherally joined in a geometric plane to the inner periphery of said ring, said backing-plate member being domed to provide a concavity which will face the laryngeal inlet, and said backing-plate member having connection means at its proximal end for airway-tube communication with said concavity, said connection means having a generally proximally directed axis which is at an acute angle to said geometric plane; said ring having an inner cross-sectional area which is substantially constant along an extended continuous arc which includes said proximal end and which further includes continuous laterally opposite side passages which extend to a location which is at a predetermined longitudinal offset that is short of said distal end, wherein said predetermined offset is in the order of twice the radial width ($R_2-R_1$) of said ring within said side passages; and flexible tubular conduit means secured to and tracking the acute-angle inclination of said airway-tube connection means, said conduit means having peripherally sealed connection to said ring at passage through a ring portion near the proximal end of said predetermined offset, and said conduit means having further peripherally sealed connection to said ring at a distal-end location of open-conduit communication distally beyond the distal end of said ring.

2. The laryngeal mask airway system of claim 1, in which said tubular conduit is of lesser external diameter than the radial width within said side passages, whereby the passing and sealing of said conduit to and through the distal end of said ring will allow passage of inflation/deflation air within said ring and on both upper and lower sides of conduit passage therethrough.

3. The laryngeal mask airway system of claim 1, in which the cross-sectional area for passage of inflation/deflation air within the distal end of said ring is at least substantially as great as within said continuous arc.

4. The laryngeal mask airway system of claim 1, in which the distal end of said tubular conduit is open along a profile of truncation which substantially accords with adjacent contouring of the distal ring opening to which said conduit is bonded.

5. The laryngeal mask airway system of claim 4, in which the bonded connection of said conduit to the distal ring opening is a circumferentially continuous elastomeric bead.

6. The laryngeal mask airway system of claim 4, in which one or more arcuate reinforcement-bead formations are on the portion of said conduit between the two locations of local conduit bonding to said ring.

7. The laryngeal mask airway system of claim 4, in which an inflatable flexible elastomeric back-cushion formation is peripherally sealed to said ring in registering overlap with said backing-plate member.

8. The laryngeal mask airway system of claim 7, in which plural longitudinally spaced arcuate reinforcement-bead formations are on the portion of said conduit in and to substantially the extent of a distal half of said ring.

9. The laryngeal mask airway system of claim 1, in which an elongate airway tube is connected to said connection means, and said airway tube is bonded to said conduit means for a preponderance of its longitudinal extent.

10. The laryngeal mask airway system of claim 9, in which said airway tube is of greater diameter than said conduit means, and in which, for the extent of airway-tube bonding to said conduit means, said conduit means is locally integrated into peripheral completion of said airway tube.

11. A laryngeal mask airway system, comprising an elongate airway tube having a distal end for insertion in a patient, a mask comprising a generally elliptical inflatable ring adapted for sealing engagement with the laryngeal inlet of a patient, a domed backing-plate member having a base which is peripherally connected in essentially a single plane to the inner periphery of said ring and having a proximal-end inlet-air connection to said airway tube on an inclined axis of inlet-air connection to said backing-plate member wherein the inclination is at an acute angle that is distally convergent to said single plane, and an elongate flexible gastric-discharge tube of smaller diameter than the inflated thickness of said ring, said gastric-discharge tube having a distal-end portion which is carried by said backing-plate member and which has sealed entrance into and exit from the distal end of said ring, the distal end of said gastric-discharge tube being truncated at a distally extending acute angle to said plane wherein said truncation is at least in part at close distal extension beyond sealed distally open emergence from passage through said ring.

12. A laryngeal mask airway system, comprising an elongate airway tube having a distal end for insertion in a patient, a mask comprising a generally elliptical inflatable ring adapted for sealing engagement with the laryngeal inlet of a patient, a domed backing-plate member having a base which is peripherally connected in essentially a single plane to the inner periphery of said ring and having a proximal-end inlet-air connection to said airway tube on an inclined axis of inlet-air connection to said backing-plate member wherein the inclination is at an acute angle that is distally convergent to said single plane, and an elongate flexible gastric-discharge tube of smaller diameter than the inflated thickness of said ring, said gastric-discharge tube having a distal-end portion which is carried by said backing-plate member and which has sealed entrance into and exit from the distal end of said ring, the distal end of said gastric-discharge tube being truncated at a distally extending acute angle to said plane at or at close distal extension beyond sealed distally open emergence from passage through said ring, said gastric-discharge tube being bonded to said airway tube for a preponderance of its length to the situs of airway-tube connection to said backing plate.

13. A laryngeal mask airway system, comprising an elongate airway tube having a distal end for insertion in a patient, a mask comprising a generally elliptical inflatable ring adapted for sealing engagement with the laryngeal inlet of a patient, a domed backing-plate member having a base which is peripherally connected in essentially a single plane to the inner periphery of said ring and having a proximal-end inlet-air connection to said airway tube on an inclined axis of inlet-air connection to said backing-plate member wherein the inclination is at an acute angle that is distally convergent to said single plane, and an elongate flexible gastric-discharge tube of smaller diameter than the inflated thickness of said ring, said gastric-discharge tube having a distal-end portion which is carried by said backing-plate member and which has sealed entrance into and exit from the distal end of said ring, the distal end of said gastric-discharge tube being truncated at a distally extending acute angle to said plane at or at close distal extension beyond sealed distally open emergence from passage through said ring, the distally expanding acute angle of truncation being in the range of 30° to 60° to said plane.

14. A laryngeal mask airway system, comprising an elongate airway tube having a distal end for insertion in a patient, a mask comprising a generally elliptical inflatable ring adapted for sealing engagement with the laryngeal inlet of a patient, a domed backing-plate member having a base which is peripherally connected in essentially a single plane to the inner periphery of said ring and having a proximal-end inlet-air connection to said airway tube on an inclined axis of inlet-air connection to said backing-plate member wherein the inclination is at an acute angle that is distally convergent to said single plane, and an elongate flexible gastric-discharge tube of smaller diameter than the inflated thickness of said ring, said gastric-discharge tube having a distal-end portion which is carried by said backing-plate member and which has sealed entrance into and exit from the distal end of said ring, the distal end of said gastric-discharge tube being truncated at a distally extending acute angle to said plane at or at close distal extension beyond sealed distally open emergence from passage through said ring, the elastomeric material of said gastric-discharge tube being softly compliant but being reinforced against circumferential collapse for substantially its entire length, except that for substantially the distal half of said mask, the gastric-discharge tube is not thus reinforced.

15. A laryngeal-mask airway system, comprising an elongate flexible airway tube having a proximal end adapted for connection to ventilating apparatus external to a patient and having a distal-masking end for insertion in the patient's anatomical airway, a flexible drainage tube of smaller diameter than the diameter of the airway tube and longitudinally integrated into a portion of the airway tube, said drainage tube having a proximal end adapted for connection to drainage apparatus external to the patient and having a distal end extending distally beyond the distal end of said airway tube;

said distal masking end comprising a generally elliptical inflatable ring adapted for sealing engagement with the patient's laryngeal inlet, a domed backing-plate member having a base which is peripherally connected in essentially a single plane to the inner periphery of said ring and having a proximal-end inlet-air connection to said backing-plate member wherein the inclination is at an acute angle that is distally convergent to said single plane, the domed portion of said backing-plate member having a slot formation with spaced slot edges at the inlet-air connection such that the portion of the drainage tube that is integrated with the distal end of the airway tube is connected and sealed to the backing-plate member along said spaced slot edges, and the distal remainder of said drainage tube passes through the distal end of said ring with sealed proximal entrance into and distal exit from the distal end of said ring.

16. The laryngeal-mask airway system of claim 15, in which the diameter of said drainage tube is at least no greater than substantially one-half the diameter of said airway tube.

17. The laryngeal-mask airway system of claim 15, in which the distal end of said discharge tube is the distal limit of said masking end and is truncated at an angle in the range 20 to 30 degrees with respect to said single plane.

18. A laryngeal mask airway system, comprising an elongate airway tube having a distal end for insertion in a patient, a mask comprising a generally elliptical inflatable ring adapted for sealing engagement with the laryngeal inlet of a patient, a domed backing-plate member having a base which is peripherally connected in essentially a single plane to the inner periphery of said ring and having a proximal-end inlet-air connection to said airway tube on an inclined axis of inlet-air connection to said backing-plate member wherein the inclination is at an acute angle that is distally convergent to said single plane, and an elongate flexible gastric-discharge tube of smaller diameter than the inflated thickness of said ring, said gastric-discharge tube being integrated into the dome of said backing-plate member and substantially tracking the acute-angle inclination of said inlet-air connection, said gastric-discharge tube having a distal-end portion which is carried by said backing-plate member and which has sealed entrance into and exit from the distal end of said ring, the distal end of said gastric-discharge tube being truncated at a distally extending acute angle to said plane at or at close distal extension beyond sealed distally open emergence from passage through said ring.

* * * * *

UNITED STATES PATENT AND TRADEMARK OFFICE
CERTIFICATE OF CORRECTION

PATENT NO. :   5,632,271
DATED       :   May 27, 1997
INVENTOR(S) :  Archibald I. J. BRAIN It is certified that error appears in the above-indentified patent and that said Letters Patent is hereby corrected as shown below:

[57]     ABSTRACT:
         Line 1,      delete "laryngeal-mark"
                      and insert therefor --laryngeal-mask--

Column 3, line 20;   after "spread" delete "$S_m$,"
                     and insert therefor --$S_1$,--
Column 3, line 44;   before "wherein" and
                     after "FIG." insert --4, --.
Column 3, line 54;   after "length" delete "$\alpha$"
                     and insert therefor --$\Delta$--
Column 4, line 51;   delete "accused incorporated," and
                     insert therefor --Accusil Incorporated--

Signed and Sealed this

Fourteenth Day of October, 1997

Attest:

BRUCE LEHMAN

Attesting Officer        Commissioner of Patents and Trademarks